United States Patent
Yamashita et al.

(10) Patent No.: US 7,138,036 B2
(45) Date of Patent: Nov. 21, 2006

(54) MONITORING DEVICE

(75) Inventors: Hiroshi Yamashita, Hiroshima-ken (JP); Setsuo Suzuki, Hiroshima-ken (JP); Hiroshi Iwata, Hiroshima-ken (JP); Toshihiro Tokudome, Aichi-ken (JP); Masayuki Ogawa, Miyazaki-ken (JP); Isao Kodaka, Tokyo (JP); Masatoshi Kaku, Aichi-ken (JP); Hisao Usogoe, Aichi-ken (JP)

(73) Assignees: Mitsubishi Heavy Industries, Ltd., Tokyo (JP); OJI Paper Co., Ltd., Tokyo (JP)

( * ) Notice: Subject to any disclaimer, the term of this patent is extended or adjusted under 35 U.S.C. 154(b) by 36 days.

(21) Appl. No.: 10/474,041

(22) PCT Filed: May 29, 2002

(86) PCT No.: PCT/JP02/05207

§ 371 (c)(1),
(2), (4) Date: Feb. 20, 2004

(87) PCT Pub. No.: WO02/097192

PCT Pub. Date: Dec. 5, 2002

(65) Prior Publication Data

US 2004/0112560 A1     Jun. 17, 2004

(30) Foreign Application Priority Data

May 30, 2001  (JP) .............................. 2001-161885

(51) Int. Cl.
*D21F 7/06* (2006.01)

(52) U.S. Cl. .................... 162/263; 162/198; 162/252; 162/DIG. 10; 162/49; 382/141; 382/149; 382/151; 100/99

(58) Field of Classification Search ................ 162/263, 162/198, 252, DIG. 10, 262; 382/141, 149, 382/151; 356/445, 36
See application file for complete search history.

(56) References Cited

U.S. PATENT DOCUMENTS 4,486,098 A * 12/1984 Buchegger et al. .......... 356/445

FOREIGN PATENT DOCUMENTS

EP         0 265 081         4/1988

(Continued)

*Primary Examiner*—Mark Halpern
(74) *Attorney, Agent, or Firm*—Armstrong, Kratz, Quintos, Hanson & Brooks, LLP (57) ABSTRACT

A monitoring apparatus is provided which can ensure the prevention of a paper break even in a poor installation environment. A light source (9) illuminates light (9a) on a lateral edge (1a) of wet paper (1) and a camera (5) captures light (9b) reflected therefrom. The camera (5) is a micro camera and completely covered by a camera box (10). The camera box (10) has an observation window (10a) which is made of a transparent member, at the lens side (5a) of the camera (5). The outer surface of the observation window (10a) is coated and an air curtain (12a) that flows from above to below prevents staining caused by mist. The air curtain (12a) is formed in such a manner that air that is continuously supplied inside a cover (11) flows along the outer surface of the observation window (10a) from an opening portion (11a). A color image obtained by the camera (5) is subjected to image processing in an image processing device (6) and the resulting image is projected on a monitor TV (7), so that variations of the release point (3) can be monitored. This allows for forecasting of a machine abnormality leading to a paper break.

7 Claims, 5 Drawing Sheets

FOREIGN PATENT DOCUMENTS

| | | |
|---|---|---|
| EP | 1002754 A1 | 5/2000 |
| JP | 3-130492 | 6/1991 |
| JP | 4-65594 | 3/1992 |
| JP | 6-59361 | 8/1994 |
| JP | 6-294092 | 10/1994 |
| JP | 7-315647 | 12/1995 |
| JP | 2000-154489 | 6/2000 |
| WO | WO 87/04248 | 7/1987 |

* cited by examiner

MONITORING DEVICE

This application is a 371 of PCT/JP02/05207 filed 29 May 2002.

TECHNICAL FIELD

The present invention relates to monitoring apparatuses for a monitoring strip-shaped object running continuously, and relates to a monitoring apparatus for monitoring, for example, the flow of paper in a paper machine.

BACKGROUND ART

For a conventional paper making machine, during operation, an operator periodically patrols and monitors it to check the operational state, so as to ensure stable operation of the machine. In order to detect the occurrence of a paper tear, for example, a paper-tear detecting sensor which is constituted by an infrared emitter arranged at the obverse side of running paper and a detector arranged at the reverse side of the running paper is installed in the machine. When the paper tears, the detector detects infrared light, so that the paper tear can be recognized.

With such a paper-tear detecting sensor, while a paper tear can be detected, its cause cannot be determined. For this reason, in recent years, a camera and a light source have been installed around the machine to monitor its state, and also, the monitored state is recorded in a video recorder or a digital memory, so that how the paper breaks can be replayed. In this manner, the operator can determine the cause. This approach, however, merely replays a recorded scene of the situation in which the paper tore, and thus cannot prevent a paper break or tear from occurring. Recently, paper machines have become increasingly faster, and thus it is important to minimize the occurrence of problems, such as paper breaks, in order to improve the production efficiency.

An approach for overcoming the above-described problems is disclosed in, for example, Japanese Unexamined Patent Application Publication No. 2000-154489. In this approach, a light source is arranged at one side of the paper surface of paper running on rolls in a paper machine and a plurality of cameras are arranged at the other side, and images of the light transmitted through the running paper from the light source are captured by the plurality of cameras. The amount of variation in release points of the running paper from a roll is quantitatively determined so that the paper machine is monitored for an abnormality.

With the above-described approach, however, release points across the entire width of the running paper are monitored by a plurality of cameras, and thus, when the image-capturing environment is poor due to, for example, the generation of a large amount of mist in the vicinity of a monitoring portion, it is difficult to determine the amount of variations in the positions of release points across the entire width. Further, since the monitoring equipment is installed at both paper surfaces of the running paper, when space for the monitoring portion is limited, it is difficult to install the monitoring equipment in practice. Although this approach is superior in that monitoring is performed using transmitted light that can provide a clearer image, it is inconvenient in practice.

DISCLOSURE OF THE INVENTION

The present invention has been made in view of the above, and an object of the present invention is to provide a monitoring apparatus that detects a running paper abnormality more reliably even in a poor installation environment, that can prevent a running paper abnormality and paper breaking from occurring. Another object of the present invention is to prevent abnormal running of a strip-shaped object flowing continuously.

The present invention has been made to overcome the above-described problems, and is characterized in that light from a light source is directed to a lateral edge of a strip-shaped object flowing continuously and is reflected, an image of the object is captured with the reflected light, and the image is subjected to image processing, thereby quantitatively monitoring the amount of variations in the running path of the object.

The present invention is applicable, for example, for monitoring a spot where paper tends to be broken in a paper machine. That is, light from the light source is illuminated on running paper in the paper machine, an image of the running paper is captured with light reflected therefrom, and the captured image is subjected to image processing, so that the amount of variations at the release point of the running paper from a roll is quantitatively monitored to diagnose abnormalities in the paper machine.

A specific configuration of the present invention includes light-emitting means for illuminating light on a lateral edge of paper running on a roll in a paper machine, image-capturing means for capturing an image of light that comes from the light-emitting means and that reflects from the lateral edge of the paper, image-processing means for processing the image captured by the image-capturing means, and diagnosing means for diagnosing an abnormality in the paper machine by quantitatively monitoring the release point of the paper from the roll for its varying positions in accordance with the result of processing by the image processing means.

The light-emitting means and the image-capturing means can be installed at only the machine side.

The present invention is particularly applicable to a case in which the image-capturing environment at the monitoring portion is poor due, for example, to the generation of mist. In this case, it is preferable to provide means for preventing staining of the light-receiving window of the image-capturing means. Further, for the light source of the light-emitting means in this case, it is preferable to use a metal-halide light source.

It is desirable to pre-set abnormality diagnosis conditions based on the amount of variations associated with an object in the normal state. When the abnormality diagnosis conditions are affected by various environmental conditions, it is preferable to change the abnormality diagnosis conditions as the environmental conditions change. For example, in the diagnosing means, the conditions for diagnosing the abnormality are adapted so as to be changeable in accordance with the basis weight and the draw amount of the paper.

It is further preferable to have a mechanism that performs automatic control for maintaining normal operation when an abnormality is diagnosed and determined. That is, adjusting means is further provided so that, when the abnormality is found, the adjusting means adjusts the draw amount in accordance with a result of the diagnosis to thereby prevent paper tear.

It is to be noted that the "basis amount" herein refers to the weight per 1 $m^2$ sheet of paper and the "draw amount"

refers to the degree of tension of the paper web between individual sections in a paper machine and is determined by speed differences among driving rolls of the individual sections in the paper machine.

BEST MODE FOR CARRYING OUT THE INVENTION

An embodiment of a monitoring apparatus according to the present invention will now be described with reference to drawings.

A description is given of a case in which a monitoring apparatus according to one embodiment of the present invention is applied to a paper machine. In this case, the monitoring apparatus monitors the operational state of the paper machine.

The paper machine generally includes a stock inlet, a wire section (wire part), a press section (press part), and a dryer section (dryer part). In addition, the paper machine typically has a calender section (calender part) and a reel section (reel part). As one example, a paper making process in the case of a Fourdrinier paper machine will be briefly described. A carefully selected pulp liquid is sprayed over an endless wire from the stock inlet. The resulting pulp is dehydrated in a suction box and is passed through a slice to have a uniform thickness. In the press section, felts are rotated in conjunction with press rolls, and, at the same time when water is squeezed, the surface of the paper is smoothed (paper web formation). Subsequently, the paper is heated and dried in the dryer section. In the calender section, the paper surface is smoothed and calendered. Lastly, the web is wound by the reel section.

Figure 1:
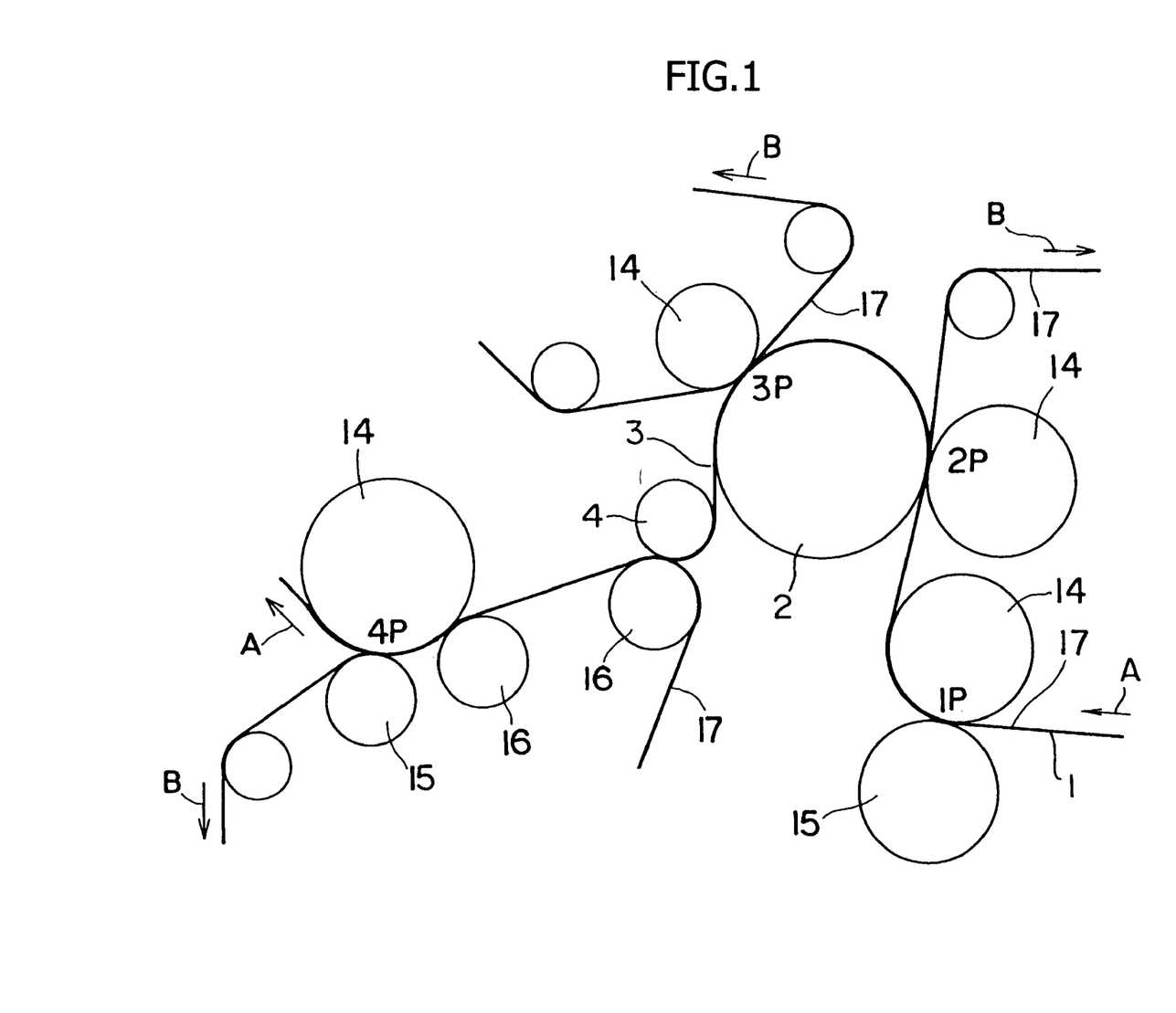
FIG. 1 is a side view schematically illustrating a press part of a paper machine to which a monitoring apparatus according to one embodiment of the present invention is applied.

The press section at which the monitoring apparatus is provided will now be described. The press section in this embodiment shown in FIG. 1 has four stages of presses, i.e., a first press (1P) to a fourth press (4P), and is provided with a center roll 2, a press top roll 14, a press bottom roll 15, a suction roll 16, and a paper roll 4. These rolls 2, 14 to 16, and 4 together with felts 17 convey wet paper 1 in the direction of arrow A. This wet paper 1 is a paper web that was formed by the wire part and that has been transferred to the press part. The felts 17 move in the directions of arrows B. To clean the center roll 2, a shower (not shown) is provided in the vicinity thereof.

Figure 2:
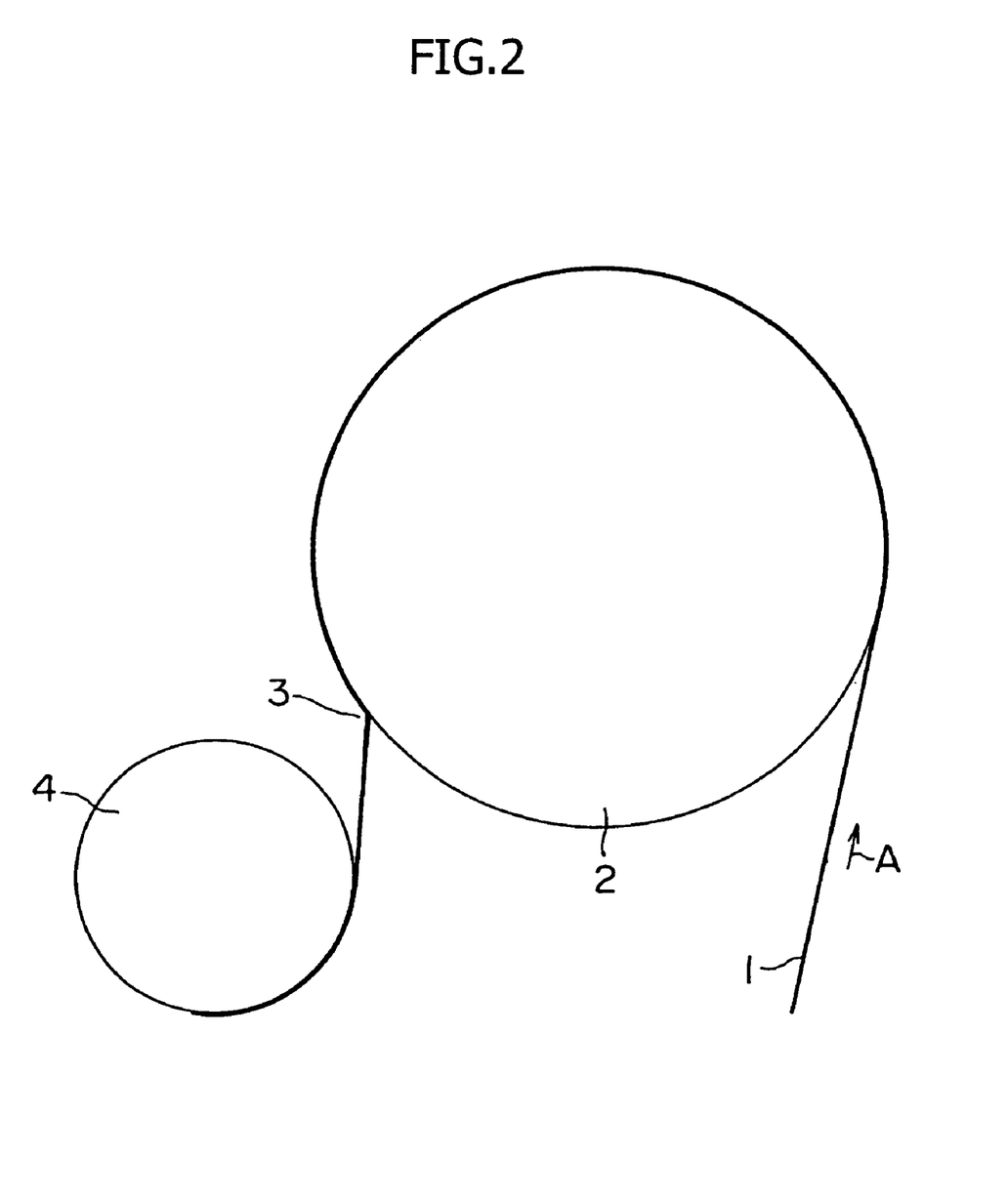
FIG. 2 is an enlarged view of the exit of a center roll in the press section shown in FIG. 1.

At the center roll portion of the press section, the wet paper 1 is separated from the felt 17, further separated (released) at the release point 3 from the surface of the center roll 2, as shown in FIG. 2, and conveyed to the next process via the paper roll 4. The wet paper 1 is not supported by the felt 17 or the like (open draw) at the release point 3, which is, therefore, a spot at which a paper is most likely to break or tear. Thus, monitoring of the release point 3 is a critical factor for stable operation while preventing paper from tearing. The monitoring apparatus according to the embodiment of the present invention monitors variable conditions at the vicinity of the release point 3. The release point 3 herein refers to a point at which an edge in the width direction of the wet paper 1 is separated from the center roll 2.

Figure 3:
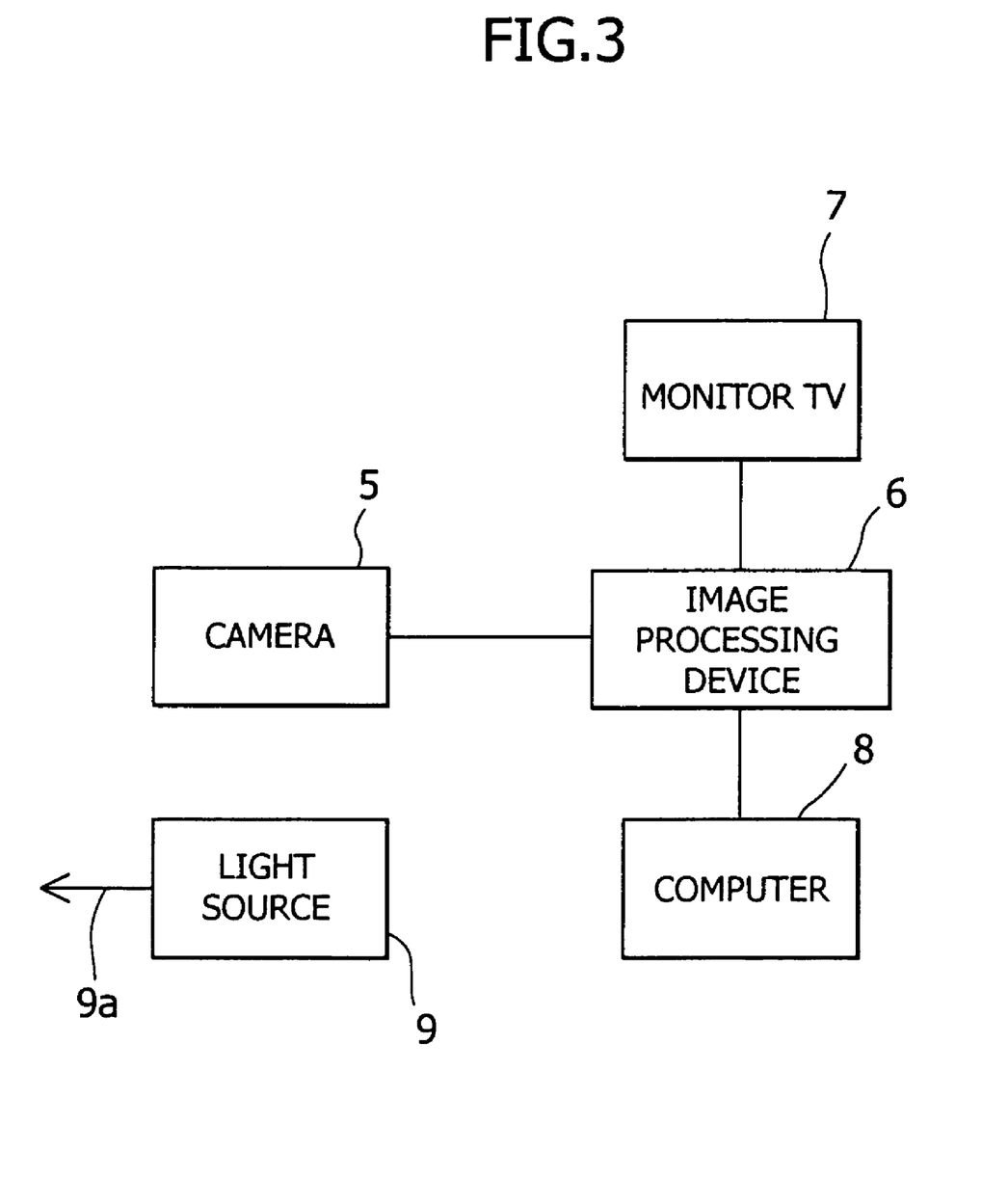
FIG. 3 is a system block diagram of the monitoring apparatus of the embodiment of the present invention.
Figure 4:
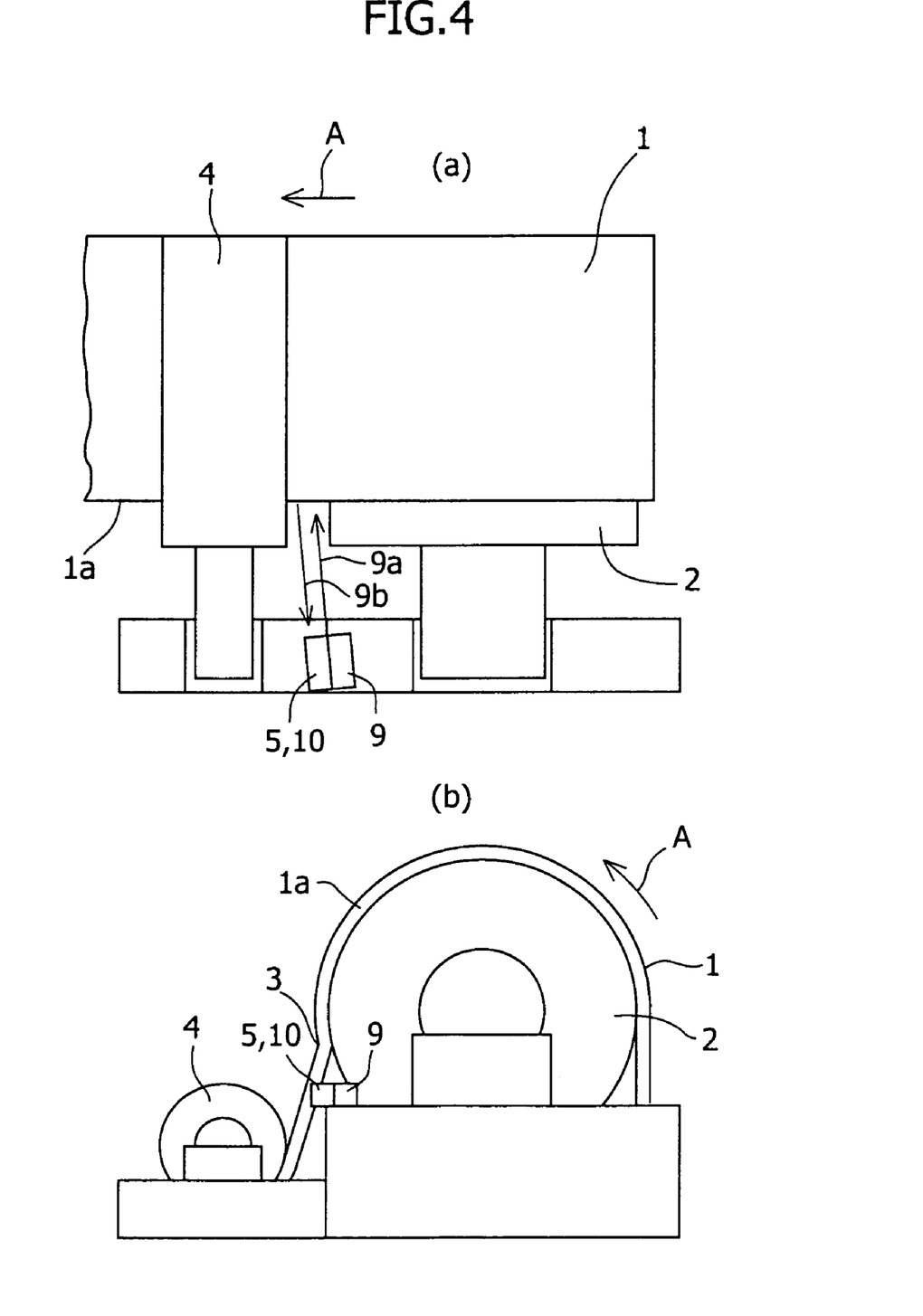
FIG. 4(a) is a plan view showing a state in which the monitoring apparatus is installed in the vicinity of the exit of the center roll shown in FIG. 2
FIG. 4(b) is a front view of the same state.
Figure 5:
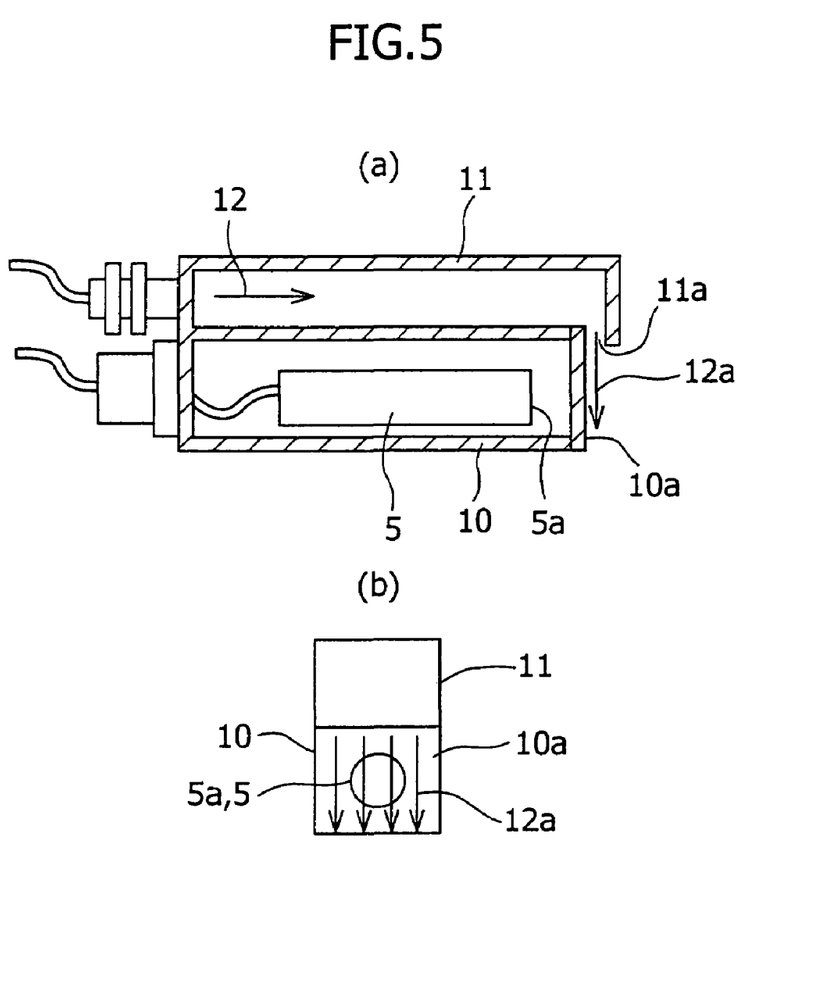
FIG. 5(a) is a longitudinal sectional view of a camera box.
FIG. 5(b) is a front view of the camera box, as viewed from an observation window side.

Individual elements of the monitoring apparatus will be described with reference to FIGS. 3 to 5. As shown in FIG. 3, the monitoring apparatus includes a camera 5, an image processing device 6, a monitor TV 7, a computer 8, and a light source 9.

The camera 5 is connected to the image processing device 6, and the image processing device 6 is connected to the monitor TV 7 and the computer 8. The light source 9 is a metal-halide light source (metal halide lamp) in this embodiment. This metal-halide light source is a high-intensity discharge lamp that emits light by discharging electricity in a mixture of metallic vapor and halide dissociation products and is a powerful light source whose wavelength distribution is flat. The use of the metal-halide light source can improve differentiation from peripheral equipment in image processing, by making good use of the fact that the wet paper 1 is white.

As shown in FIGS. 4(a) and 4(b), the camera 5 is provided at the same position as the light source 9, and both the light-emitting surface of the light source 9 and the lens of the camera 5 are directed to a lateral edge 1a of the wet paper 1. Thus, the light source 9 illuminates light 9a on the lateral edge 1a of the wet paper 1 and the camera 5 captures light 9b reflected therefrom. This camera 5 is completely covered by a camera box 10, as shown in FIGS. 5(a) and 5(b). This camera box 10 has an observation window 10a which is made of a transparent member on the lens side 5a of the camera 5, so that the camera 5, even in the camera box 10, can capture external light.

The outer surface of the observation window 10a is covered with a coating for stain prevention, and the mechanism illustrated below further prevents the observation window 10a from staining. Namely, a cover 11 having an opening portion 11a is attached to the upper side of the observation window 10a of the camera box 10. Air 12 is continuously supplied inside the cover 11, so that an air gap, i.e., an air curtain 12a flowing from above to below, is formed at the outer surface of the observation window 10a. This air curtain 12a serves to prevent mist or the like from attaching to the outer surface of the observation window 10a, thereby making it possible to remove or reduce an obstruction caused by mist when the camera 5 captures an image. As described above, while the coating and the air curtain 12a are used in this embodiment to prevent mist attachment and to remove attached mist, the present invention is not limited thereto. For example, the arrangement may be such that a wiper (now shown) is used to wipe off mist attached to the outer surface of the observation window 10a. Alternatively, the arrangement may be such that the observation window 10a is rotated to generate a centrifugal force, thereby removing attached mist. The camera 5 is a micro color-CCD camera which thus allows for a reduction in the outside dimensions of the camera box 10. This reduces the space for installation, thereby allowing for installation in places where space is tight. Further, the size of the observation window 10a is reduced, thereby allowing for a reduction in the proportion of staining due to mist attachment.

It should be noted that the mist is generated by the shower (not shown) for cleaning the center roll 2, as described above, and additionally, the mist is generated by a doctor (not shown) provided at the center roll 2. Thus, an anti-mist measure is important for release-point monitoring by the camera 5.

While the combination of the camera 5 and the light source 9 is arranged at the machine side in this embodiment, the present invention is not limited thereto. Thus, the combinations may be arranged at both the machine side and an operation side so as to monitor the edges at both sides. When they are arranged on both machine and operation sides, there is a concern that light from the light source at one side may enter the camera on the other side. Even in this case, however, since the wet paper 1 generally has a width of as much as a few meters, the camera is not affected by light from the light source at the other side. Processing of an image obtained in this manner will now be described. A color image obtained by the camera 5 is analyzed by the image processing device 6, and unwanted lines are eliminated. That is, a monochrome image is extracted from the color image by using a green component, and a noise component is removed from the monochrome image. Thereafter, the lateral edge of the wet paper 1 is emphasized using a spatial filter and binarized. A roll portion in the image is registered as a mask image and a crease at the release point of the lateral edge 1a is extracted from the binary image from which the mask image is removed. This image processing is simple and involves an efficient algorithm; therefore, it can be executed at a high speed and can also analyze the frequency of variations at the lateral edge.

After image processing, an image is output to the monitor TV 7 (see FIG. 3). The image on the monitor TV 7 provides the same viewpoint as that of an operator performing visual monitoring, and therefore the operator feels familiar and comfortable.

A graph obtained from the above-described processing will now be described with reference to FIG. 6. In this figure, the vertical axis indicates the amount of variation from a reference and the horizontal axis indicates time (s).

Figure 6:
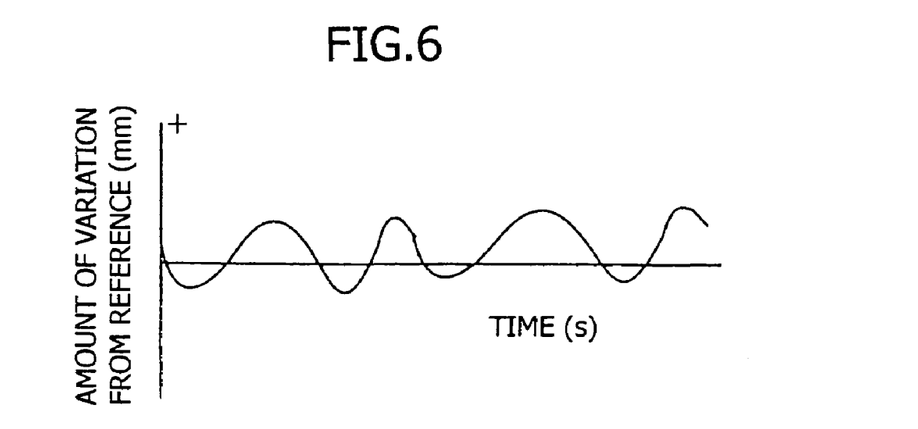
FIG. 6 is a graph showing a release-point variation obtained from an image processing device, the vertical axis indicating the amount of variation from a reference and the horizontal axis indicating time (s).

The release point 3 of the wet paper 1 varies as shown in FIG. 6, from the graph of which the state of variations can be determined. Thus, allowable values (abnormality diagnosis conditions) of the amount and period of variations at the release point 3 can be set in the computer 8 (see FIG. 3). The settings of those abnormality diagnosis conditions can be appropriately changed depending on the basis weight and the draw amount of the paper. In this embodiment, while the computer 8 has a function (diagnosing means) for diagnosing an abnormality in the paper machine by quantitatively monitoring the amount of variation in the release point, the diagnosing means may be provided separately from the computer 8. In this manner, a machine abnormality leading to a paper break can be forecast. When an abnormal event occurs, for example, an alarm or the like can also be set off to notify the operator of the abnormal event, so that the draw amount can be changed so as to prevent a paper break. That is, the press part can be controlled by adjusting the draw amount so as to adjust the shape of the profile. The amount of variation in the release point is important in forecasting a paper break and can be used to prevent a paper break. The configuration may be such that the adjustment of the draw amount is automatically controlled by adjusting means (not shown) connected to the computer 8.

In addition, based on the amount of variations at the release point, the replacement time of parts, such as the felt, can be determined. Immediately after replacement of the felt, when the draw is constant, the dehydration state is poor so that the release point fluctuates. The release point is controlled to a constant release position by changing the draw. The felt settles in two or three days, thus improving the dehydration state, and the release position is set in place by changing the draw. When the paper machine is operated under these conditions, the dehydration state begins to deteriorate at a certain time to cause the release point to fluctuate. This commonly results in earlier replacement of parts. Accordingly, staining and the surface condition of the replaced felt are quantitatively analyzed and are compiled into a database together with the draw amount and the amount of variation in the release point. This allows for determination of adequate replacement time considering both the paper quality and economical factors such as the cost of parts.

Thus, it is possible to support stable operation and to determine the cause of a paper break, since the position of the release point and the margin and period of the variation thereof are strongly correlated with the draw, staining of the paper machine and parts, and a change in raw material. In conjunction with the need for higher-speed paper machines in recent years, the operation process and management for stain prevention as well as mechanical stability have become important, and the present invention can reliably cope with the need.

INDUSTRIAL APPLICABILITY

In a monitoring apparatus according to the present invention, light from a light source is illuminated on a lateral edge of a strip-shaped object running continuously and is reflected, an image of the object is captured with the reflected light, and the image is subjected to image processing, thereby quantitatively monitoring an amount of variations in the running path of the object. This allows for continuous recognition of changes in the running object and allows for accurate monitoring.

A monitoring apparatus according to the present invention includes light-emitting means for shining light on a lateral edge of paper running on a roll in a paper machine, image-capturing means for capturing an image of light that is illuminated by the light-emitting means and that is reflected by the lateral edge of the paper, image-processing means for processing the image captured by the image-capturing means, and diagnosing means for diagnosing an abnormality in the paper machine by quantitatively monitoring the amount of variations at the release point of the paper from the roll in accordance with the result of processing by the image processing means. This allows for continuous recognition of changes in the path of the running paper and allows for accurate monitoring.

Installation of the light-emitting means and the image-capturing means at only the machine side does not provide an obstacle to visual observation and operation by the operator since there is no need to install those means at the operation side, which can improve the usability and operability.

Further providing means for preventing staining of the light-receiving window of the image-capturing means can remove or reduce an obstacle in capturing an image to thereby provide a satisfactory image.

The use of a metal-halide light source as the light source for the light-emitting means can improve differentiation from peripheral equipment at the time of image processing, thereby allowing for accurate monitoring even in a poor image-capturing environment.

In the diagnosing means, setting the conditions for diagnosing an abnormality so as to be changeable in accordance with the basis weight and the draw amount of the paper can improve the diagnostic accuracy, thereby allowing for optimal monitoring.

Further providing an adjusting means which adjusts the draw amount in accordance with the result of the diagnosis of the abnormality can adjust the shape of the profile so as to prevent paper tear and control the press part and the like.

The invention claimed is:

1. A monitoring apparatus characterized by comprising light-emitting means for shining light on a lateral edge of paper running on a roll in a paper machine;
   image-capturing means, completely covered by the box, having a light receiving window, for capturing an image of light that is shined by the light-emitting means and that is reflected by the lateral edge of the paper;
   means for preventing staining of the light receiving window of the box;
   image-processing means for processing the image captured by the image-capturing means; and
   diagnosing means for diagnosing an abnormality in the paper machine by quantitatively monitoring an amount of variation in a release point of the paper from the roll in accordance with a result of processing by the image processing means.

2. The monitoring apparatus according to claim 1, characterized in that the light-emitting means and the image-capturing means are provided only at a machine side.

3. The monitoring apparatus according to claim 1, characterized in that a metal-halide light source is used as a light source for the light-emitting means.

4. The monitoring apparatus according to any one of claims 1, 2 and 3, characterized in that in the diagnosing means, conditions for diagnosing the abnormality are changeable in accordance with a basis weight and a draw amount of the paper.

5. The monitoring apparatus according to claim 4, characterized by further comprising adjusting means, wherein, when the abnormality is diagnosed, the adjusting means adjusts the draw amount in accordance with a result of the diagnosis, thereby preventing a paper tear.

6. The monitoring apparatus according to claim 1, characterized in that the means for preventing staining of the light receiving window of the box is an air curtain flowing across the outer surface of the window.

7. The monitoring apparatus according to claim 1, characterized in that the means for preventing staining of the light receiving window of the box is a coating covering the outer surface of the window.

* * * * *